United States Patent
Quackenbush et al.

(10) Patent No.: US 7,157,900 B2
(45) Date of Patent: Jan. 2, 2007

(54) REMOVABLE BREAKING CALIBRATION CONNECTOR FOR TOROIDAL CONDUCTIVITY SENSOR AND METHOD OF CALIBRATION

(75) Inventors: John K. Quackenbush, Middleboro, MA (US); Stephen B. Talutis, Milton, MA (US)

(73) Assignee: Invensys Systems Inc., Foxboro, MA (US)

( * ) Notice: Subject to any disclaimer, the term of this patent is extended or adjusted under 35 U.S.C. 154(b) by 0 days.

(21) Appl. No.: 11/065,788

(22) Filed: Feb. 25, 2005

(65) Prior Publication Data
US 2005/0189936 A1 Sep. 1, 2005

Related U.S. Application Data

(60) Provisional application No. 60/548,924, filed on Feb. 27, 2004.

(51) Int. Cl.
*G01R 31/28* (2006.01)
(52) U.S. Cl. .................................................. 324/158.1
(58) Field of Classification Search ................ 324/445, 324/765, 158.1, 72.5; 439/189, 207, 208
See application file for complete search history.

(56) References Cited

U.S. PATENT DOCUMENTS

| | | | |
|---|---|---|---|
| 4,026,620 A | 5/1977 | Lieberman | |
| 5,061,196 A | 10/1991 | Weston et al. | |
| 5,124,661 A | 6/1992 | Zelin et al. | |
| 5,201,668 A | 4/1993 | Endo et al. | |
| 5,233,860 A | 8/1993 | Mori et al. | |
| 5,262,732 A * | 11/1993 | Dickert et al. | 324/672 |
| 5,341,102 A * | 8/1994 | Akiyama et al. | 324/445 |
| 5,346,405 A | 9/1994 | Mosser, III et al. | |
| 5,660,567 A | 8/1997 | Nierlich et al. | |
| 5,690,893 A * | 11/1997 | Ozawa et al. | 422/67 |
| 6,072,313 A * | 6/2000 | Li et al. | 324/230 |
| 6,254,411 B1 | 7/2001 | Chapman et al. | |

\* cited by examiner

*Primary Examiner*—Ha Tran Nguyen
*Assistant Examiner*—Tung X. Nguyen
(74) *Attorney, Agent, or Firm*—David Barron, Esq.; Sampson & Assoc. P.C.

(57) ABSTRACT

This invention relates to electrical connectors used with non-invasive toroidal conductivity sensors and calibration thereof. A removable breaking calibration connector is provided for temporary insertion in the electrical circuit to selectively break connection to a sense toroid for zero out calibration in situ while retaining connection to the drive toroid and other peripherals, even when process fluid is flowing in the pipes.

10 Claims, 1 Drawing Sheet

REMOVABLE BREAKING CALIBRATION CONNECTOR FOR TOROIDAL CONDUCTIVITY SENSOR AND METHOD OF CALIBRATION

RELATED APPLICATION DATA

The present application claims benefit of 60/548,924 filed on Feb. 27, 2004.

FIELD OF INVENTION

The present invention relates generally to toroidal conductivity sensors and more particularly to connectors therefor, including removable breaking calibration connector portions for calibration thereof.

BACKGROUND OF INVENTION

Toroidal electrodeless conductivity (EC) sensors are used to measure conductivity in a process fluid by use of electromagnetic cores, i.e., toroids. At least two toroids are typically used, one being a 'drive' toroid and the other being a 'sense' toroid. The sensor unit applies current to the drive toroid, which in turn induces a current in the sense toroid, through a current induced in the process fluid. The current induced in the sense toroid is proportional to the conductivity of the process fluid passing through the process pipe and through the toroids.

The toroidal conductivity sensors have been one of the industry standards for a long time. Until recently most of the toroidal sensors were invasive in nature, that is, the sensor protruded into the process flow. This has worked well in the industry for many years in many applications. However, in some applications the invasive nature of such toroidal EC sensors presents an undesirable impediment of the process flow. This impediment may be particularly problematic in applications in which the process flow is relatively thick and/or viscous, which tend to generate buildup around the sensor, which in turn, may lead to erroneous conductivity measurements.

Recently, flowthrough-type EC sensors have been developed to overcome the abovementioned problems associated with the use of invasive type toroidal conductivity sensors. An example of a sensor of this type is known as the 871FT™ toroidal electrodeless conductivity (EC) sensor available from Invensys Systems, Inc. (Foxboro, Mass.) in which the sensor portion is external to the process flow.

However, currently available industrial toroidal EC sensors are typically installed by hand-wiring the sensors either to an analyzer or junction box, e.g., using hand tools. A drawback of this approach is that this installation is relatively labor intensive, and there is a possibility that such hand-wiring may be performed incorrectly.

Moreover, in most industrial installations, the cable connecting the sensor to the analyzer or junction box is disposed within electrical conduit to prevent possible degradation of the cable either through weathering or exposure to many of the harsh chemicals used in the process industry. In many instances these sensors are located far away, sometimes at a distance of up to 30 m or more, from the analyzer. In these situations, if the sensor is to be removed for replacement, often some or all of the wiring needs to be removed and then reinstalled, causing undesirable delays and costs associated with process down-time.

These toroidal EC sensors also need to calibrated from time to time. For this purpose, toroidal EC sensors such as the aforementioned 871FT™ device, may be provided with calibration ports. These ports enable a user to input a specific known conductivity value to the sensor which may then be detected by the sensor in a conventional manner. However, in order to calibrate the process for low-end conductivity and/or to zero out the sensor, the process pipe typically needs to be drained completely of any process fluid. In an application in which the process pipe extends vertically, draining may be relatively easy to carry out. However, in an application with horizontal mounting, unless the process pipe is pitched, nominally the only way to accomplish the zero reading is to uninstall the unit and then thoroughly dry the inside of the process pipe. This may be relatively difficult and potentially hazardous, e.g., in the event the process fluid is caustic or otherwise aggressive. In either case, such emptying or drying of the process pipe of the process fluid poses a problem to the user because it generally requires that the process be shut-down, thereby increasing the cost of production.

Hence there is a need for a method of quickly replacing a sensor inline and for effecting low-end calibration of conductivity sensors without interrupting the production process.

SUMMARY

One aspect of the present invention includes a toroidal conductivity sensor assembly including a toroidal conductivity sensor having a drive toroid and a sense toroid. The sensor is configured for disposition in-situ within a process flow path. An analyzer is configured to control operation of the sensor, and a multiple conductor cable communicably couples the sensor to the analyzer. A multiple conductor connector releasably couples a sensor end of the cable to the sensor, and includes a male portion and a female portion configured for mutual, releasable engagement. The connector also includes an intermediate calibration portion configured for being interposed between the male and female portions in communicable engagement therewith. The calibration portion blocks electric signals between the analyzer and the sense toroid, and passes electric signals between the analyzer and the drive toroid, and is configured for being temporarily interposed between the male and female portions to effect zero out calibration of the sensor.

Another aspect of the invention includes a removable breaking calibration connector portion for effecting zero out calibration in-situ for a toroidal conductivity sensor having a drive toroid and a sense toroid disposed in communication with an analyzer. The breaking calibration connector portion includes first and second interfaces configured for communicable engagement with the analyzer and sensor. Circuit elements are disposed electrically between the first and second interfaces, and are configured to temporarily block electric signals between the analyzer and the sense toroid. The circuit elements as also configured to pass electric signals between the analyzer and the drive toroid. The calibration portion thus permits zero out calibration of the sensor without emptying the sensor of process fluid.

A still further aspect of the invention includes a method of calibrating a toroidal connectivity sensor having a drive toroid and a sense toroid. The method includes unmating male and female portions of a multiple conductor connector, and temporarily disposing and mating the previously mentioned calibration connector portion intermediately between the male and female portions, respectively, so that the breaking calibration connector portion restores connection between the analyzer and the drive toroid and other peripheral devices, and breaks connection between the analyzer and the sense toroid. The method further includes carrying out zero out calibration of the toroidal conductivity sensor using the analyzer, removing the breaking calibration connector portion, and mating the male and female portions, so that zero out calibration for the toroidal conductivity sensor is effected.

A yet further aspect of the invention includes a connector for communicably coupling an electronic analyzer to a toroidal conductivity sensor having a drive toroid and a sense toroid. The connector includes multiple conductor connector portions disposed to releasably couple a sensor end of a multiple conductor cable to the sensor, the connector portions including a male portion and a female portion configured for mutual, releasable engagement. An intermediate calibration portion is configured for being interposed between the male and female portions in communicable engagement therewith, and is configured to block electric signals between the analyzer and the sense toroid, and to pass electric signals between the analyzer and the drive toroid. The calibration portion is configured for being temporarily interposed between the male and female portions to effect zero out calibration of the sensor.

BRIEF DESCRIPTION OF DRAWINGS

A more complete understanding of the invention and a fuller appreciation of the many attendant advantages thereof will be derived by reference to the following detailed description when considered in connection with the accompanying drawings wherein.

Figure 3:
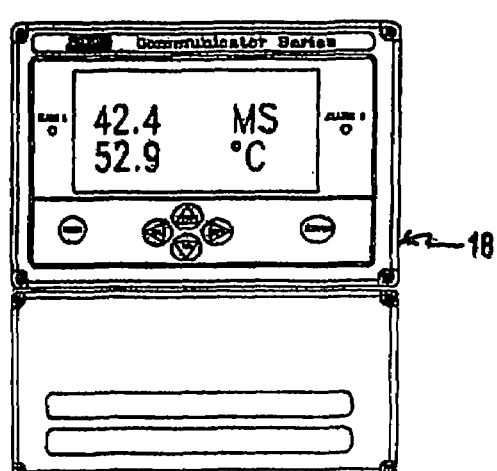
FIG. 3 is a schematic, exploded view of a third connector portion disposed between the connector portions of FIGS. 1 and 2.
Figure 3:
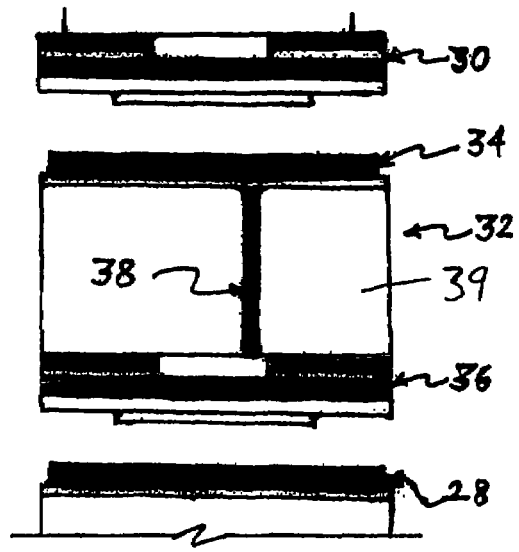

List of parts:

| Number | Nomenclature of the part |
|---|---|
| 10 | drive toroid |
| 12 | sense toroid |
| 14 | toroidal conductivity sensor |
| 16 | process flow pipe |
| 18 | analyzer/transmitter |
| 20 | sensor cable |
| 22 | sensor end of sensor cable 20 |
| 24 | analyzer end of sensor cable 20 |
| 26 | connector |
| 28 | male portion of connector 26 |
| 30 | female portion of connector 26 |
| 32 | breaking calibration connector |
| 34 | male portion of breaking calibration connector 32 |
| 36 | female portion of breaking calibration connector 32 |
| 38 | electrical conducting path only for analyzer, drive toroid and other peripherals |
| 39 | insulator |
| 40 | calibration port |

DETAILED DESCRIPTION

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. The following detailed description is, therefore, not to be taken in a limiting sense, and the scope of the present invention is defined by the appended claims and their equivalents. For clarity of exposition, like features shown in the accompanying drawings are indicated with like reference numerals and similar features as shown in alternate embodiments in the drawings are indicated with similar reference numerals.

Figure 2:
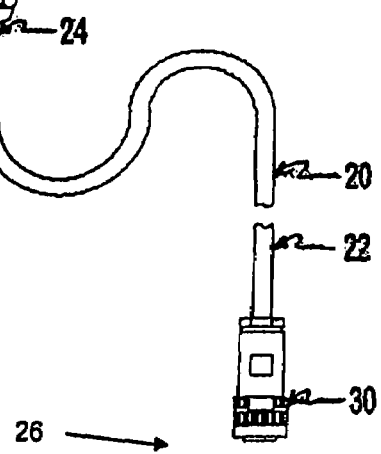
FIG. 2 is a schematic view, on an enlarged scale, of the connector portions of FIG. 1, in a mated configuration.
Figure 2:
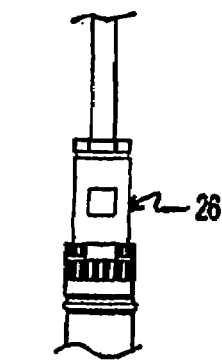
Figure 1:
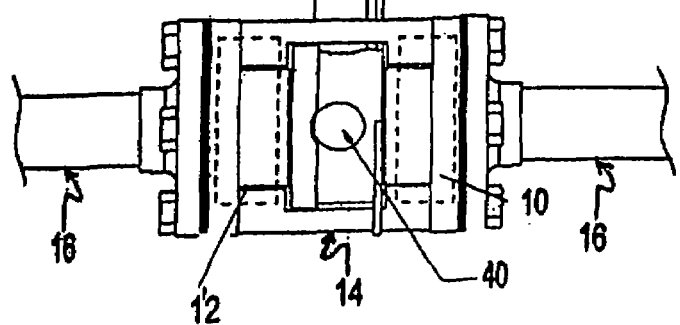
FIG. 1 is a schematic view of an embodiment of the present invention, with two connector portions in an unmated configuration.

Referring to FIGS. 1 and 2, a toroidal conductivity sensor 14, which includes a drive toroid 10 and a sense toroid 12, is disposed along a process flow pipe 16. During operation, a process fluid flows through the flow pipe 16 and through a flow path defined by sensor 14, which extends through the toroids 10, 12.

Sensor 14 is connected to an analyzer (which, as used herein, also refers to a transmitter) 18 by a sensor cable 20, having a sensor end 22 for connecting to the sensor 14 and an analyzer end 24 for connecting to an analyzer/transmitter 18. Moreover, embodiments of the invention include a multiple contact connector 26 to permit convenient replacement and/or calibration of sensor 14, as discussed in greater detail hereinbelow. Connector 26 may include nominally any suitable commercially available connector, such as the RO4 series™ miniature circular waterproof connectors available from Tajimi Electronics Co., Ltd (Tokyo, Japan).

Connector 26 includes matable portions, shown unmated in FIG. 1 and mated in FIG. 2. For convenience, these portions are respectively described herein as male and female portions 28 and 30. In the embodiment shown, portion 28 is coupled to sensor 14 either directly or via a portion of cable 20, as discussed hereinbelow, while portion 30 is coupled to analyzer/transmitter 18 via a majority of cable 20. The skilled artisan will recognize that the orientation of connector portions 28 and 30 is a matter of choice, and may be reversed, e.g., with portion 28 coupled to analyzer/transmitter 18, and portion 30 coupled to sensor 14.

Connector 26 may be disposed at nominally any convenient location along cable 20, though in desired embodiments is disposed at the sensor end of cable 20 (e.g., closer to sensor 14 than to analyzer 18). Alternatively, connector 26 may be disposed further upstream (i.e., towards analyzer/transmitter 18) on the sensor cable 20, so that a portion of cable 20 is disposed upstream, and a portion is disposed downstream, of the connector.

The connector 26 permits the customer to quickly replace the sensor 14 and/or the analyzer/transmitter 18 in the event of a failure or scheduled maintenance, to advantageously eliminate or reduce down-time and costs associated therewith.

Turning now to FIG. 3, connector 26 may be provided with a third portion, referred to herein as a breaking calibration connector 32, configured for being temporarily disposed intermediately between the male portion 28 and the female portion 30 of the connector 26. In the embodiment shown, a female portion 36 of calibration connector 32 may be mated with the male portion 28 of the connector 26 and a male portion 34 of calibration connector 32 may be mated with the female portion 30 of connector 26.

The breaking calibration connector 32 is constructed so that when installed, it selectively electrically isolates a portion of the sensor 14 from analyzer/transmitter 18, while connecting other portions thereto. When installed, calibration connector 32 electrically isolates the sense toroid 12 by effectively blocking the electrical conducting path between toroid 12 and analyzer 18. Connector 32 accomplishes this by inserting an electrical insulator 39 between otherwise matable electrical conductors connector portions 28 and 30 associated with toroid 12.

At the same time, calibration connector 32 effectively inserts electrical conductors 38 (FIG. 3) between other matable contacts of connector portions 28 and 30. In this manner, while toroid 12 is electrically isolated, the other portions of sensor 14, including drive toroid 10 and any other peripheral devices such as temperature probes and the like, may operate in a conventional manner.

Calibration connector portion 32 thus enables one to carry out a 'zero out' and/or low-end calibration of sensor 14 in-situ, that is without removing the sensor 14 from the process fluid pipe or having to empty the pipe 16. This is accomplished by letting analyzer/transmitter 18 believe it is coupled to a fully functional sensor 14 (by virtue of its connection 38 to drive toroid 10, etc.,) while detecting the same lack of signal from sense toroid 12 that it would otherwise detect in the event pipe 16 were empty.

Once 'zero out' calibration is completed, breaking calibration connector 32 may be removed and portions 28 and 30 of connector 26 re-connected to one another, to restore continuity, and thus normal operation, of both toroids 10 and 12.

Additional calibrations, such as full or mid-scale calibration may be completed in a conventional manner, such as by applying a known conductivity value (e.g., a value higher than that provided by the particular fluid currently disposed within conduit 16), to calibration port 40 (FIG. 1). Those skilled in the art will recognize that these additional calibrations may be accomplished by coupling a conventional decade box or one or more discrete resistors to calibration port 40.

Although the calibration connector 32 is shown and described as a hardware device, those skilled in the art should recognize that connector 32 may be implemented in software or a combination of hardware and software without departing from the spirit and scope of the present invention.

Similarly, although sensor 14 and analyzer 18 have been shown and described as being communicably coupled to one another by hardwire (cable 20), it should be understood that such connection may be effected wirelessly, e.g., using conventional Wi-Fi (802.11x) or Bluetooth™ technology, without departing from the spirit and scope of the invention. In this regard, connector 32 may be operationally disposed between the sensor and its wireless connection, or between the analyzer and its wireless connection. Alternatively, connector 32 may be wirelessly interposed between sensor 14 and analyzer 18, to selectively prevent signals from passing between the analyzer and the sense toroid as described herein.

Furthermore, although connector 32 has been shown and described as being physically separable from male and female connector portions 28 and 30 of connector 26, the skilled artisan should recognize that connector 32 may be disposed integrally with connector 26, e.g., to either portion 28 or portion 30, and simply actuated when desired by suitable switch means, without departing from the spirit and scope of the invention.

Having described embodiments of the invention, the following is a description of an exemplary method of use thereof. Referring to Table I, a method is provided for calibrating a toroidal connectivity sensor 14. This method includes unmating 52 male and female portions 28 and 30 of connector 26, and temporarily mating 54 calibration connector 32 intermediately therebetween, to restore connection between analyzer 18 and drive toroid 10 (and any other devices) and break connection between analyzer 18 and sense toroid 12. Zero out calibration of the toroidal conductivity sensor 14 is then carried out 56 using analyzer 18, followed by removal 58 of the connector 32 and re-mating 60 male and female portions 28 and 30. Optionally, one or more known conductivity values may be applied 62 to a calibration port 40 of sensor 14, followed by non-zero calibration 64 of sensor 14 using the analyzer.

TABLE I 52 unmating male and female portions 28 and 30 of connector 26
54 temporarily disposing and mating calibration connector 32 intermediately between male and female portions 28 and 30, to restore connection between analyzer 18 and drive toroid 10 (and any other devices), and breaks connection between analyzer 18 and sense toroid 12
56 carrying out zero out calibration
58 removing connector 32
60 re-mating connector 26
62 optionally applying known conductivity value(s) to a calibration port 40
64 carrying out non-zero calibration of the toroidal conductivity sensor 14 using the analyzer.

While the above description contains many specificities, these should not be construed as limitations in the scope of the invention, but rather as an exemplification of one or more desired embodiments thereof. Accordingly, the scope of the invention should be determined not by the embodiments illustrated, but by the appended claims and their equivalents.

The invention claimed is:

1. A removable breaking calibration connector portion for effecting zero out calibration in-situ for a toroidal conductivity sensor having a drive toroid and a sense toroid disposed in communication with an analyzer, the breaking calibration connector portion comprising:
   a first interface configured for communicable engagement with one of the analyzer and sensor;
   a second interface configured for communicable engagement with the other of the analyzer and sensor;
   circuit elements disposed electrically between said first and second interfaces, said circuit elements configured to temporarily block electric signals between said analyzer and said sense toroid, and to pass electric signals between said analyzer and said drive toroid;
   wherein said calibration portion permits zero out calibration of the sensor without emptying the sensor of process fluid.

2. The calibration connector portion of claim 1, comprising:
   a multiple conductor connector having male and female portions;
   said male and female portions configured for mutual, releasable engagement;
   one of said male and female portions communicably coupled to the analyzer, and the other of said male and female portions communicably coupled to the sensor;
   said first and second interfaces configured for engagement with said male and female portions to effectively interpose said calibration connector portion in communicable engagement therewith.

3. The calibration connector portion of claim 2, wherein the analyzer is communicably coupled to the sensor by a multiple conductor cable, and said multiple conductor connector is configured to releasably couple a sensor end of the cable to the sensor.

4. The calibration connector portion of claim 2, configured for being temporarily interposed between said male and female portions to effect zero out calibration of said sensor.

5. The calibration connector portion of claim 2, wherein said first and second interfaces comprise male portion which is matable with said female portion of said multiple conductor connector, and a female portion which is matable with said male portion of said multiple conductor connector.

6. The calibration connector portion of claim 2, wherein said circuit elements comprise one or more electrical conductors which permit electrical signals to pass therethrough between the analyzer and the drive toroid, and one or more electrical insulators which block electric signals between the analyzer and the sense toroid.

7. The calibration connector portion of claim 6, wherein said one or more electrical conductors are disposed to provide an electrically conductive path to the drive toroid of the toroidal conductivity sensor and other peripheral devices, the conducting path being aligned with conductors of said multiple conductor connector.

8. The calibration connector portion of claim 7, wherein said one or more electrical insulators comprise a gap between conductors of said multiple conductor connector associated with electrical signal conduction between the sense toroid and the analyzer.

9. The calibration connector portion of claim 1, comprising the toroidal conductivity sensor.

10. The calibration connector portion of claim 9, comprising the analyzer.

* * * * *